(12) United States Patent
Kim et al.

(10) Patent No.: US 9,728,293 B2
(45) Date of Patent: Aug. 8, 2017

(54) X-RAY SYSTEM, SEMICONDUCTOR PACKAGE, AND TRAY HAVING X-RAY ABSORPTION FILTER

(71) Applicants: Sang-Young Kim, Cheonan-si (KR); Kyung-Soo Rho, Suwon-si (KR); Ho-Jeong Moon, Daejeon (KR); Hyuck Shin, Bucheon-si (KR); Sun-Nyeong Jung, Asan-si (KR)

(72) Inventors: Sang-Young Kim, Cheonan-si (KR); Kyung-Soo Rho, Suwon-si (KR); Ho-Jeong Moon, Daejeon (KR); Hyuck Shin, Bucheon-si (KR); Sun-Nyeong Jung, Asan-si (KR)

(73) Assignee: SAMSUNG ELECTRONICS CO., LTD. (KR)

( * ) Notice: Subject to any disclaimer, the term of this patent is extended or adjusted under 35 U.S.C. 154(b) by 277 days.

(21) Appl. No.: 14/455,858

(22) Filed: Aug. 8, 2014

(65) Prior Publication Data
US 2015/0103974 A1    Apr. 16, 2015

(30) Foreign Application Priority Data
Oct. 16, 2013   (KR) .................. 10-2013-0123584

(51) Int. Cl.
*G01N 23/02* (2006.01)
*G21K 1/10* (2006.01)
*G01N 23/04* (2006.01)
*H01L 21/66* (2006.01)

(52) U.S. Cl.
CPC ............... *G21K 1/10* (2013.01); *G01N 23/04* (2013.01); *H01L 22/12* (2013.01)

(58) Field of Classification Search
CPC .......... G21K 1/10; G01N 23/04; H01L 22/12
See application file for complete search history.

(56) References Cited

U.S. PATENT DOCUMENTS

| 6,751,294 | B1 | 6/2004 | Blish li et al. |
| 7,072,447 | B2 | 7/2006 | Graf et al. |
| 7,315,611 | B2 | 1/2008 | Cho et al. |
| 7,763,394 | B2 | 7/2010 | Stehle |
| 8,031,840 | B2 | 10/2011 | Thran et al. |
| 8,184,776 | B2 | 5/2012 | Yuan |
| 2010/0246775 | A1* | 9/2010 | Yuan ................ G21K 1/10 378/158 |

FOREIGN PATENT DOCUMENTS

JP   2008261650 A   10/2008

* cited by examiner

*Primary Examiner* — Courtney Thomas
(74) *Attorney, Agent, or Firm* — Renaissance IP Law Group LLP

(57) ABSTRACT

An X-ray source is disposed and a detector is disposed adjacent to the X-ray source. A test specimen holder is disposed between the X-ray source and the detector. A filter is disposed between the X-ray source and the test specimen holder. The filter has a plate-shaped semiconductor, a granular semiconductor, or a combination thereof.

14 Claims, 21 Drawing Sheets

X-RAY SYSTEM, SEMICONDUCTOR PACKAGE, AND TRAY HAVING X-RAY ABSORPTION FILTER

CROSS-REFERENCE TO RELATED APPLICATION

This application claims priority under 35 U.S.C. §119 to Korean Patent Application No. 10-2013-0123584 filed on Oct. 16, 2013, the disclosure of which is hereby incorporated by reference in its entirety.

BACKGROUND

1. Technical Field

Embodiments of the inventive concept relate to an X-ray system, a semiconductor package, and a tray having an X-ray absorption filter.

2. Description of Related Art

A technique of testing a semiconductor package and a set board having the semiconductor package using an X-ray system is being studied.

SUMMARY

Embodiments of the inventive concept provide an X-ray system capable of reducing degradation of a semiconductor device and obtaining a clear image.

Another embodiment of the inventive concept provides a semiconductor package capable of reducing degradation of the semiconductor device due to X-rays.

Still another embodiment of the inventive concept provides a tray for a semiconductor device capable of reducing degradation of semiconductor device due to X-rays.

The technical objectives of the inventive concept are not limited to the above disclosure, and other objectives may become apparent to those of ordinary skill in the art based on the following descriptions.

Embodiments of the inventive concept provide an X-ray system. The X-ray system includes an X-ray source and a detector adjacent to the X-ray source. A test specimen holder is disposed between the X-ray source and the detector. A filter is disposed between the X-ray source and the test specimen holder. The filter includes a plate-shaped semiconductor, a granular semiconductor, or a combination thereof.

In another embodiment, the filter may include Si, Ge, GaAs, InP, InGaAs, InGaAsP, or a combination thereof.

In still another embodiment, the plate-shaped semiconductor may include a semiconductor wafer.

In yet another embodiment, the test specimen holder may serve to load a semiconductor package. The filter may include the same or substantially the same material as a semiconductor substrate in the semiconductor package.

In yet another embodiment, the filter may have a greater thickness than that of the semiconductor substrate in the semiconductor package.

In yet another embodiment, the filter may be formed in the semiconductor package. The filter may be disposed between the X-ray source and the semiconductor substrate.

In yet another embodiment, a tray may be disposed on the semiconductor package. The tray may be disposed between the X-ray source and the semiconductor package. The filter may be formed in the tray or on the surface of the tray.

In yet another embodiment, the filter may include a metal filter including Zn, Fe, Al, Cu, Ni, Zr, Mo, Mn, V, or a combination thereof. The metal filter is formed on one surface of the plate-shaped semiconductor.

Embodiments of the inventive concept provide a semiconductor package. The semiconductor package includes a semiconductor filter adjacent to the semiconductor chip.

In another embodiment, the semiconductor filter may have the same or substantially the same material as a semiconductor substrate in the semiconductor chip.

In still another embodiment, a semiconductor oxide film configured to cover the surface of the semiconductor filter may be disposed.

In yet another embodiment, an encapsulant configured to cover the semiconductor chip may be formed. The semiconductor filter may include a granular semiconductor. The granular semiconductor may be included in the encapsulant.

In yet another embodiment, a package substrate may be attached to the semiconductor chip. The semiconductor filter may include a plate-shaped semiconductor. The plate-shaped semiconductor may be formed in the package substrate or on the surface of the package substrate.

In yet another embodiment, the plate-shaped semiconductor may be formed between the package substrate and the semiconductor chip.

In yet another embodiment, a through electrode electrically connected to the package substrate and the semiconductor chip passing through the plate-shaped semiconductor may be formed.

In yet another embodiment, an underfill layer or an adhesive film may be formed between the package substrate and the semiconductor chip. The semiconductor filter may include a granular semiconductor. The granular semiconductor may be included in the underfill layer or the adhesive film.

In yet another embodiment, a coating film configured to cover the semiconductor chip may be formed. The granular semiconductor may be included in the coating film.

Furthermore, embodiments of the inventive concept provide a tray. The tray includes a plurality of cavities on which a semiconductor package is seated. Sidewalls configured to separate the cavities from each other are provided. A lower plate exposed on the bottom of the cavities is provided. A semiconductor filter is disposed adjacent to the cavities.

In another embodiment, the semiconductor filter may include the same or substantially the same material as a semiconductor substrate in the semiconductor package.

In still another embodiment, the semiconductor filter includes a plate-shaped semiconductor, a granular semiconductor, or a combination thereof.

In yet another embodiment, the granular semiconductor is included in the lower plate.

In yet another embodiment, the granular semiconductor may be attached onto the surface of the lower plate.

In yet another embodiment, the plate-shaped semiconductor may be attached to the surface of the lower plate.

In yet another embodiment, the plate-shaped semiconductor is inserted into the lower plate.

Details of other embodiments are included in the detailed description and drawings.

BRIEF DESCRIPTION OF THE DRAWINGS

The foregoing and other features and advantages of the inventive concepts will be apparent from the more particular description of preferred embodiments of the inventive concepts, as illustrated in the accompanying drawings in which like reference characters refer to the same or substantially the same parts throughout the different views. The drawings are not necessarily to scale, emphasis instead being placed upon illustrating the principles of the inventive concepts. In the drawings.

DETAILED DESCRIPTION OF THE EMBODIMENTS

Figure 1:
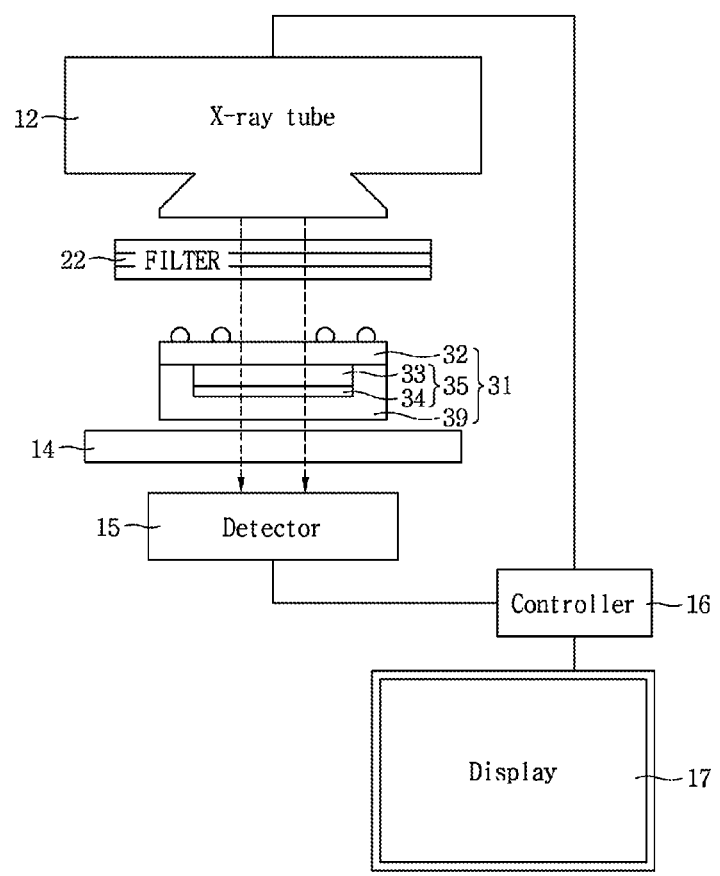
FIGS. 1 to 3 are schematic configuration views illustrating an X-ray system in accordance with embodiments of the inventive concept.

Various embodiments will now be described more fully with reference to the accompanying drawings in which some embodiments are shown. These inventive concepts may, however, be embodied in different forms and should not be construed as limited to the embodiments set forth herein. Rather, these embodiments are provided so that this disclosure is thorough and complete and fully conveys the inventive concept to those skilled in the art. In the drawings, the sizes and relative sizes of layers and regions may be exaggerated for clarity.

It will be understood that when an element or layer is referred to as being "on," "connected to" or "coupled to" another element or layer, it can be directly on, connected or coupled to the other element or layer or intervening elements or layers may be present. In contrast, when an element is referred to as being "directly on," "directly connected to" or "directly coupled to" another element or layer, there are no intervening elements or layers present. Like numerals refer to like elements throughout. As used herein, the term "and/or" includes any and all combinations of one or more of the associated listed items.

It will be understood that, although the terms first, second, third, etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present inventive concept.

Spatially relative terms, such as "beneath," "below," "lower," "above," "upper" and the like, may be used herein for ease of description to describe one element's or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" can encompass both an orientation of above and below. The device may be otherwise oriented (rotated 90 degrees or at other orientations) and the spatially relative descriptors used herein interpreted accordingly.

The terminology used herein is for the purpose of describing particular embodiments only and is not intended to be limiting of the present inventive concept. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Embodiments are described herein with reference to cross-sectional illustrations that are schematic illustrations of idealized embodiments (and intermediate structures). As such, variations from the shapes of the illustrations as a result, for example, of manufacturing techniques and/or tolerances, are to be expected. Thus, embodiments should not be construed as limited to the particular shapes of regions illustrated herein but are to include deviations in shapes that result, for example, from manufacturing. For example, an implanted region illustrated as a rectangle will, typically, have rounded or curved features and/or a gradient of implant concentration at its edges rather than a binary change from implanted to non-implanted region. Likewise, a buried region formed by implantation may result in some implantation in the region between the buried region and the surface through which the implantation takes place. Thus, the regions illustrated in the figures are schematic in nature and their shapes are not intended to illustrate the actual shape of a region of a device and are not intended to limit the scope of the present inventive concept.

Terms such as "front side" and "back side" may be used in a relative sense herein to facilitate easy understanding of the inventive concept. Accordingly, "front side" and "back side" may not refer to any specific direction, location, or component, and may be used interchangeably. For example, "front side" may be interpreted as "back side" and vice versa. Also, "front side" may be expressed as "first side," and "back side" may be expressed as "second side," and vice versa. However, "front side" and "back side" cannot be used interchangeably in the same embodiment.

The term "near" is intended to mean that one among two or more components is located within relatively close proximity of a certain other component. For example, it should be understood that when a first end is near a first side, the first end may be closer to the first side than a second end, or the first end may be closer to the first side than to a second side.

Unless otherwise defined, all terms (including technical and scientific terms) used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Figure 2:
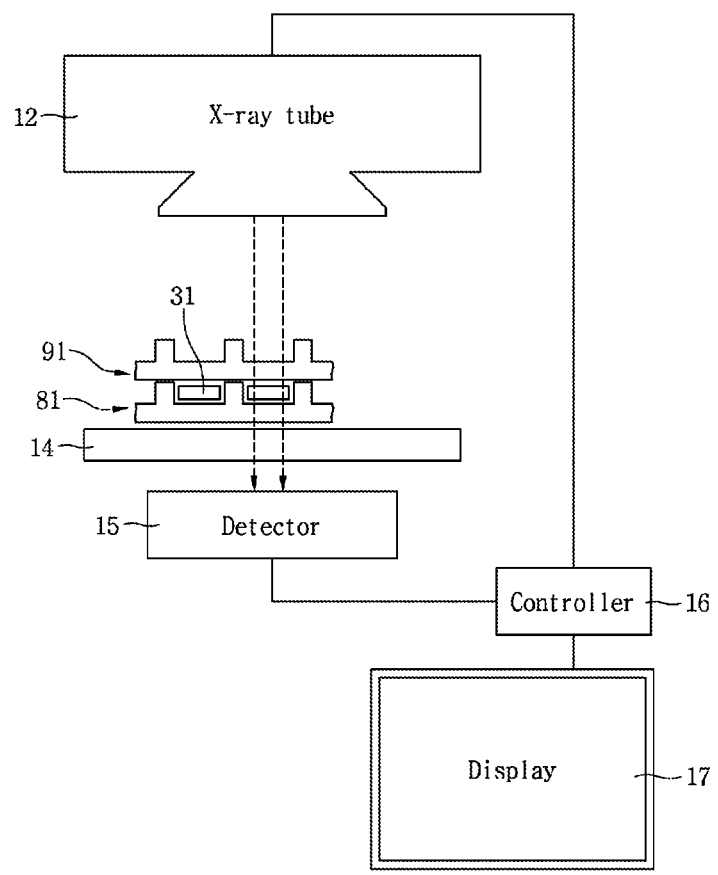
Figure 3:
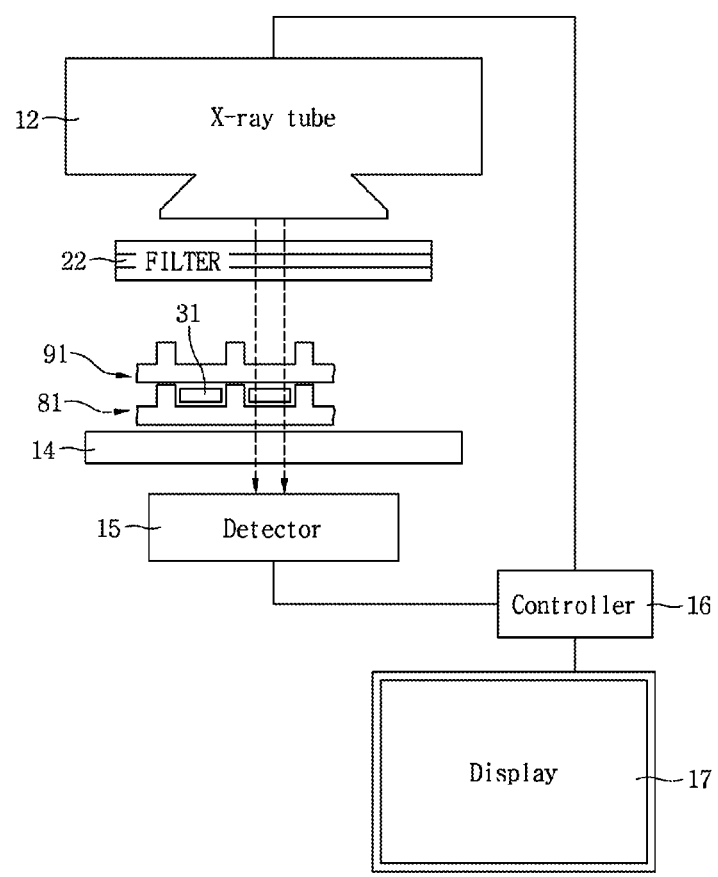

FIGS. 1 to 3 are schematic views of exemplary configurations of an X-ray system in accordance with some embodiments of the inventive concepts. The X-ray system according to some embodiments of the inventive concept may be a device for testing a semiconductor package or a set board having the semiconductor package.

Referring to FIG. 1, a detector 15 may be disposed adjacent to an X-ray source, for example, an X-ray tube 12. A test specimen holder 14 may be disposed between the X-ray tube 12 and the detector 15. A filter 22 may be disposed between the X-ray tube 12 and the test specimen holder 14. The X-ray tube 12 and the detector 15 may be connected to a controller 16. A display 17 may be connected to the detector 15 through the controller 16. A semiconductor package 31 may be loaded onto the test specimen holder 14.

In some embodiments, instead of the X-ray tube 12 shown in FIG. 1, other types of X-ray sources/generators are used to implement the concepts of the present disclosure.

The semiconductor package 31 may include a package substrate 32, a semiconductor chip 35, and an encapsulant 39. The semiconductor chip 35 may include a semiconductor substrate 33 having an active region 34 thereon. Although a plurality of active and/or passive devices and insulating layers may be formed in the active region 34, but the detailed description thereof will be omitted for the sake of brevity. The test specimen holder 14 may be a device which can move the semiconductor package 31 to the left, right, up, or down, and/or rotate the semiconductor package 31. The test specimen holder 14 may be a part of a transportation device, such as a belt conveyer.

In some embodiment, the enapsulant 39 may be formed of a conventional molding material such as an epoxy molding compound. However, the encapsulant 39 may be other suitable encapsulants, e.g., a ceramic casing.

The filter 22 may include the same or substantially the same material as the semiconductor substrate 33. The filter 22 may include Si, Ge, GaAs, InP, InGaAs, InGaAsP, or a combination thereof. For example, the semiconductor substrate 33 may be a silicon wafer, and the filter 22 may include silicon. The semiconductor substrate 33 may include GaAs, and the filter 22 may include GaAs. The filter 22 may include a plate-shaped semiconductor (or semiconductor plate), a granular semiconductor or semiconductor particles, or a combination thereof. The filter 22 may be referred to as a semiconductor filter. The filter 22 may have a greater thickness than the semiconductor substrate 33.

In another embodiment, the filter 22 may further include a metal filter including Zn, Fe, Al, Cu, Ni, Zr, Mo, Mn, V, or a combination thereof.

X-rays radiated from the X-ray tube 12 may sequentially pass through the filter 22 and the semiconductor package 31, and the detector 15 may detect the X-rays. The display 17 may display an image converted from a signal detected in the detector 15. The X-rays radiated from the X-ray tube 12 may show various wavelengths and intensity. The X-rays radiated from the X-ray tube 12 may include a first wavelength region required to obtain an image, and a second wavelength region absorbed into the semiconductor substrate 33 and degrades characteristics of the semiconductor chip 35.

For example, the X-rays radiated from the X-ray tube 12 may have a wavelength of about 0.01 nm to about 1100 nm. The X-rays radiated from the X-ray tube 12 may include a hard X-ray showing a wavelength of about 0.01 nm to about 10 nm and an intensity of about 12 KeV to about 120 KeV, a soft X-ray having a wavelength of about 10 nm to about 100 nm and an intensity of about 0.1 KeV to about 12 KeV. The hard X-ray may correspond to the first wavelength region, and the soft X-ray may correspond to the second wavelength region. The hard X-ray may be used for obtaining an image, and the soft X-ray may be absorbed into the semiconductor substrate 33, and cause various failures, such as degradation of refresh characteristics or a charge loss in the semiconductor chip 35.

The semiconductor filter 22 may transmit X-rays in the first wavelength region required to obtain an image, and absorb and/or shield X-rays in the second wavelength region which degrade the characteristics of the semiconductor chip 35. The filter 22 may transmit the hard X-ray and absorb the soft X-ray. In other words, the filter 22 may substantially prevent the transmission of the soft X-ray.

In still another embodiment, the semiconductor package 31 may include a semiconductor filter formed of the same or substantially the same material as the semiconductor substrate 33. The semiconductor filter included in the semiconductor package 31 may include a plate-shaped semiconductor, a granular semiconductor, or a combination thereof. The semiconductor filter included in the semiconductor package 31 may include Si, Ge, GaAs, InP, InGaAs, InGaAsP, or a combination thereof. The semiconductor filter included in the semiconductor package 31 may transmit X-rays in the first wavelength region required to obtain an image, and absorb and/or shield X-rays in the second wavelength region which degrade the characteristics of the semiconductor chip 35. The semiconductor filter included in the semiconductor package 31 may transmit the hard X-ray and absorb the soft X-ray.

Referring to FIG. 2, a first tray 81, a semiconductor package 31, and a second tray 91 may be loaded onto a test specimen holder 14. The semiconductor package 31 may be loaded between the first tray 81 and the second tray 91. The second tray 91 may be disposed between an X-ray tube 12 and the semiconductor package 31. The first tray 81 and the second tray 91 may include a semiconductor filter formed of the same or substantially the same material as the semiconductor substrate 33 in the semiconductor package 31. The semiconductor filter included in the first tray 81 and the second tray 91 may include a plate-shaped semiconductor or a semiconductor object having one or more substantially flat surfaces, a granular semiconductor, or any combination thereof. The semiconductor filter included in the first tray 81 and the second tray 91 may include Si, Ge, GaAs, InP, InGaAs, InGaAsP, or a combination thereof.

The semiconductor filter included in the first tray 81 and the second tray 91 may transmit X-rays in a first wavelength region required to obtain an image, and absorb and/or shield X-rays in the second wavelength region which degrade the characteristics of the semiconductor package 31. The semiconductor filter included in the first tray 81 and the second tray 91 may transmit the hard X-ray and absorb the soft X-ray.

Referring to FIG. 3, a filter 22 may be disposed between an X-ray tube 12 and a test specimen holder 14. A first tray 81, a semiconductor package 31, a second tray 91 may be loaded onto the test specimen holder 14. The filter 22 may be disposed between the X-ray tube 12 and the second tray 91.

The filter 22 may include a semiconductor filter having the same or substantially the same material as a semiconductor substrate 33 in the semiconductor package 31. The semiconductor package 31 may include a semiconductor filter formed of the same or substantially the same material as the semiconductor substrate 33 in the semiconductor package 31. The first tray 81 and the second tray 91 may include a semiconductor filter formed of the same or substantially the same material as the semiconductor substrate in the semiconductor package 31.

Figure 4:
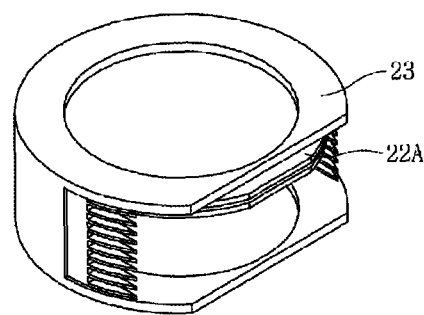
FIG. 4 is a perspective view illustrating a filter in accordance with embodiments of the inventive concept.
Figure 5:
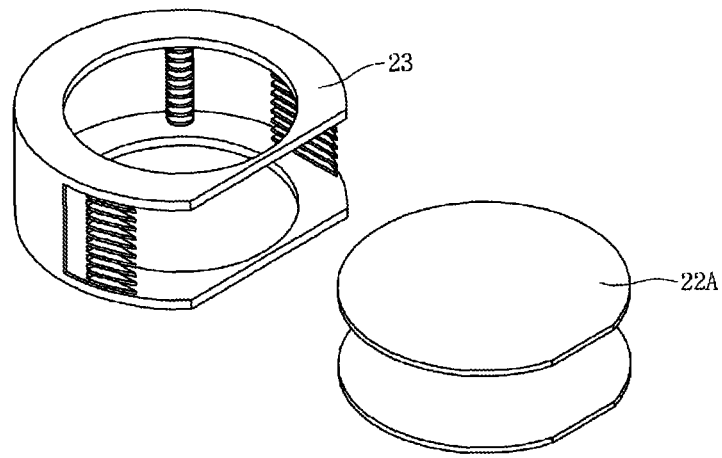
FIG. 5 is an exploded perspective view of FIG. 4.

FIG. 4 is a perspective view illustrating a filter in accordance with some embodiments of the inventive concept, and FIG. 5 is an exploded perspective view of FIG. 4.

Referring to FIGS. 4 and 5, a plurality of plate-shaped filters 22A may be inserted into a filter case 23. Each of the plate-shaped filters 22A may include a plate-shaped semiconductor. Each of the plate-shaped filters 22A may include Si, Ge, GaAs, InP, InGaAs, InGaAsP, or a combination thereof. For example, each of the plate-shaped filters may be a semiconductor wafer. Each of the plate-shaped filters 22A may be a silicon wafer or a silicon on insulator (SOI) wafer.

In another embodiment, one or more plate-shaped filters 22A, for example, ten plate-shaped filters 22A may be inserted into the filter case 23.

Figure 6:
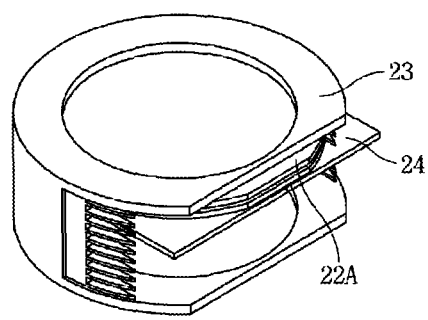
FIG. 6 is a perspective view illustrating a filter in accordance with embodiments of the inventive concept.
Figure 7:
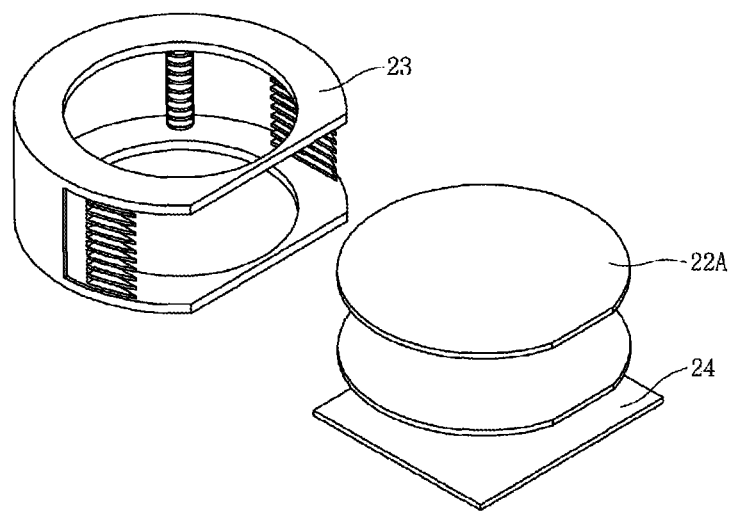
FIG. 7 is an exploded perspective view of FIG. 6.

FIG. 6 is a perspective view illustrating a filter in accordance with some embodiments of the inventive concepts, and FIG. 7 is an exploded perspective view of FIG. 6.

Referring to FIGS. 6 and 7, a plurality of plate-shaped filters 22A and a metal filter 24 may be inserted into a filter case 23. The metal filter 24 may include Zn, Fe, Al, Cu, Ni, Zr, Mo, Mn, V, or a combination thereof.

Figure 8:
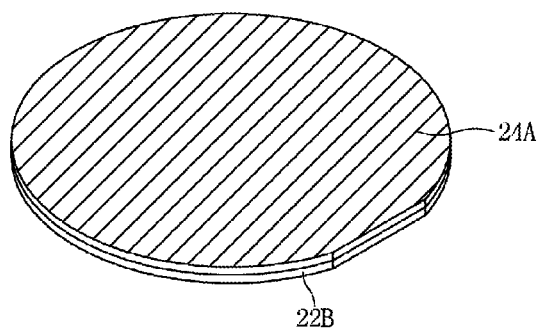
FIG. 8 is a perspective view illustrating a filter in accordance with embodiments of the inventive concept.
Figure 9:
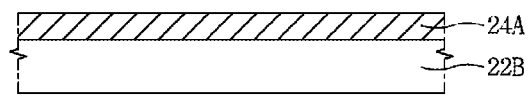
FIGS. 9 and 10 are cross-sectional views of FIG. 8.
Figure 10:
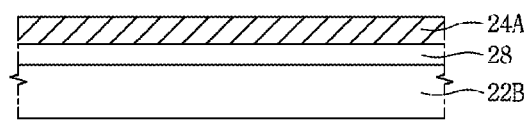

FIG. 8 is a perspective view illustrating a filter in accordance with some embodiments of the inventive concepts, and FIGS. 9 and 10 are cross-sectional views of FIG. 8.

Referring to FIGS. 8 and 9, a metal filter 24A may be formed on a plate-shaped filter 22B. The plate-shaped filter 22B may be a plate-shaped semiconductor, such as a semiconductor wafer. The metal filter 24A may be formed on one surface of the plate-shaped filter 22B. The metal filter 24A may be in contact with one surface of the plate-shaped filter 22B. The metal filter 24A may have a smaller thickness than the plate-shaped filter 22B. The plate-shaped filter 22B may include Si, Ge, GaAs, InP, InGaAs, InGaAsP, or a combination thereof. The metal filter 24A may include Zn, Fe, Al, Cu, Ni, Zr, Mo, Mn, V, or a combination thereof.

Referring to FIGS. 8 and 10, an insulating layer 28 (not shown in FIG. 8) and a metal filter 24A may be formed on the plate-shaped filter 22B. The insulating layer 28 may be disclosed between the plate-shaped filter 22B and the metal filter 24A. The insulating layer 28 may be in contact with both the plate-shaped filter 22B and the metal filter 24A. The insulating layer 28 may be formed of silicon oxide.

Figure 11:
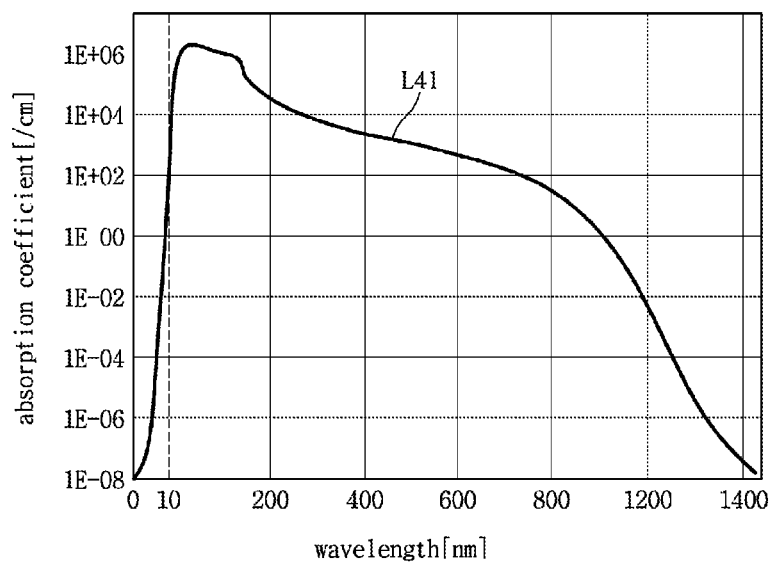
FIG. 11 is a graph showing an absorption coefficient of silicon.

FIG. 11 is a graph showing an absorption coefficient of silicon.

Referring to FIG. 11, a curve L41 is a line which indicates an absorption coefficient of silicon versus wavelength. As shown in the curve L41, silicon shows a high absorption coefficient at wavelengths of 10 nm to 1100 nm.

Figure 12:
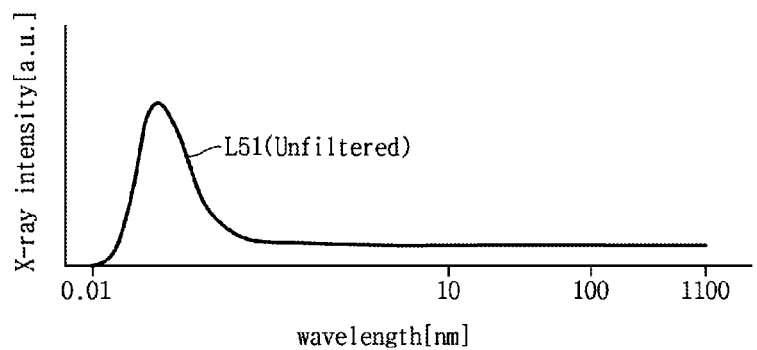
FIGS. 12 and 13 are graphs showing X-ray intensity versus wavelength.
Figure 13:
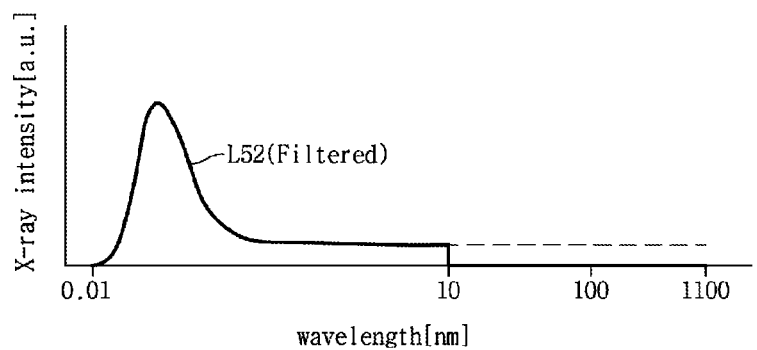

FIGS. 12 and 13 are graphs showing X-ray intensity on the y-axis versus wavelength on the x-axis.

Referring to FIG. 12, a curve L51 indicates intensity of X-rays radiated from an X-ray tube versus wavelength when a filter is not used. As shown in the curve L51, due to the characteristics of the X-ray tube, X-rays having a wavelength of 0.01 nm to 1100 nm or more may be radiated.

Referring to FIG. 13, a curve L52 indicates intensity of X-rays irradiated to a sample versus wavelength when a filter is used. As shown in the curve L52, due to the absorption characteristics of a filter, the X-rays having a wavelength of 10 nm to 1100 nm may be removed. The X-rays having a wavelength of 0.01 nm to 10 nm may be extracted using a filter in accordance with some embodiments of the inventive concepts, and irradiated to a sample.

Figure 14:
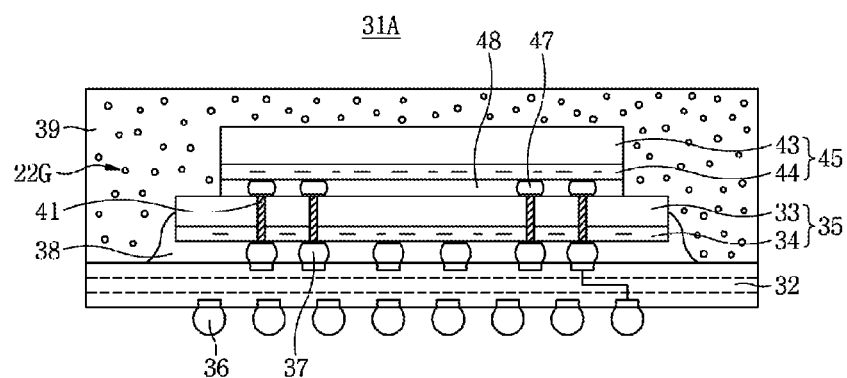
FIG. 14 is a cross-sectional view illustrating a semiconductor package in accordance with embodiments of the inventive concept.
Figure 15:
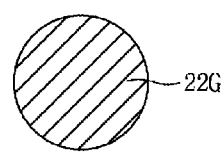
FIGS. 15 and 16 are cross-sectional views illustrating a granular filter in accordance with embodiments of the inventive concept.
Figure 16:
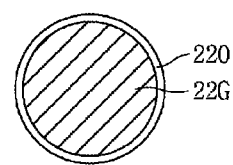

FIG. 14 is a cross-sectional view of a semiconductor package in accordance with some embodiments of the inventive concepts, and FIGS. 15 and 16 are cross-sectional views of a granular filter in accordance with some embodiments of the inventive concepts.

Referring to FIG. 14, a semiconductor package 31A may include a package substrate 32, a first semiconductor chip 35, a second semiconductor chip 45, and an encapsulant 39. The first semiconductor chip 35 may include a first semiconductor substrate 33 and a first active region 34 on the first semiconductor substrate 33. A plurality of active and/or passive devices and insulating layers may be formed on the first active region 34. The second semiconductor chip 45 may include a second semiconductor substrate 43 and a second active region 44 on the second semiconductor substrate 43. A plurality of active and/or passive devices and insulating layers may be formed on the second active region 44. A plurality of granular filters 22G may be included in the encapsulant 39.

The first semiconductor substrate 33 and the second semiconductor substrate 43 may include Si, Ge, GaAs, InP, InGaAs, InGaAsP, or a combination thereof. For example, the first semiconductor substrate 33 and the second semiconductor substrate 43 may be a semiconductor wafer, such as a single crystalline silicon wafer or SOI wafer. The second semiconductor substrate 43 may be the same or substantially the same type of semiconductor wafer as the first semiconductor substrate 33, and the second semiconductor substrate 43 may be a different type of semiconductor wafer from the first semiconductor substrate 33.

The encapsulant 39 may cover the first semiconductor chip 35 and the second semiconductor chip 45. Each of the granular filters 22G may include a granular semiconductor formed of the same or substantially the same material as the first semiconductor substrate 33 or the second semiconductor substrate 43. For example, the first semiconductor substrate 33 and the second semiconductor substrate 43 may be a silicon wafer, and each of the granular filters 22G may include one or more silicon granules that may include, for instance, a single silicon particle or multiple silicon particles clustered together. The first semiconductor substrate 33 or the second semiconductor substrate 43 may include GaAs, and each of the granular filters 22G may include GaAs. The granular filters 22G may be included in the encapsulant 39. The granular filters 22G and filler (not illustrated) may be included in the encapsulant 39. The granular filters 22G may be included in the encapsulant 39 instead of the filler. The granular filters 22G may shield X-ray having a wavelength region easily absorbed into the first semiconductor substrate 33 and the second semiconductor substrate 43.

The package substrate 32 may be a rigid printed circuit board, a flexible printed circuit board, or a rigid-flexible printed circuit board. External terminals 36 may be formed on the bottom surface of the package substrate 32. The external terminals 36 may be a solder ball, a conductive bump, a conductive tap, a conductive spacer, a lead grid array (LGA), a pin grid array (PGA), or a combination thereof.

First through electrodes 41 passing through the first semiconductor chip 35 may be formed. First internal terminals 37 and a first adhesive film 38 may be formed between the first semiconductor chip 35 and the package substrate 32. The first internal terminals 37 may be a solder ball or a conductive bump. The first adhesive film 38 may include an underfill layer. The first internal terminals 37 may be connected to the first through electrodes 41 and the package substrate 32 through the first adhesive film 38.

The second semiconductor chip 45 may be mounted on the first semiconductor chip 35. Second internal terminals 47 and a second adhesive film 48 may be formed between the first semiconductor chip 35 and the second semiconductor chip 45. The second adhesive film 48 may include a tape-type material film, a liquid-coating-curing material film, or a combination thereof. The second adhesive film 48 may be referred to as a die attach film (DAF) or non-conductive film (NCF).

The second semiconductor chip 45 may show a different horizontal width from the first semiconductor chip 35. The second semiconductor chip 45 may have a smaller horizontal width than the first semiconductor chip 35. The second semiconductor chip 45 may be a different type from the first semiconductor chip 35. For example, the first semiconductor chip 35 may be a logic chip, and the second semiconductor chip 45 may be a memory chip.

Referring to FIG. 15, a granular filter 22G may include a granular semiconductor. The granular semiconductor may include Si, Ge, GaAs, InP, InGaAs, InGaAsP, or a combination thereof. The granular filter 22G may have various shapes, such as a circle, an oval, a polygon, an amoeba, or any combination thereof.

Referring to FIG. 16, a semiconductor oxide film 220 may substantially surround a granular filter 22G. For example, the granular filter 22G may be a silicon grain, and the semiconductor oxide film 220 may be a silicon oxide film. The semiconductor oxide film 220 may be in direct contact with a surface of the granular filter 22G.

FIGS. 17 to 29 are cross-sectional views illustrating a semiconductor package in accordance with some embodiments of the inventive concepts.

Figure 17:
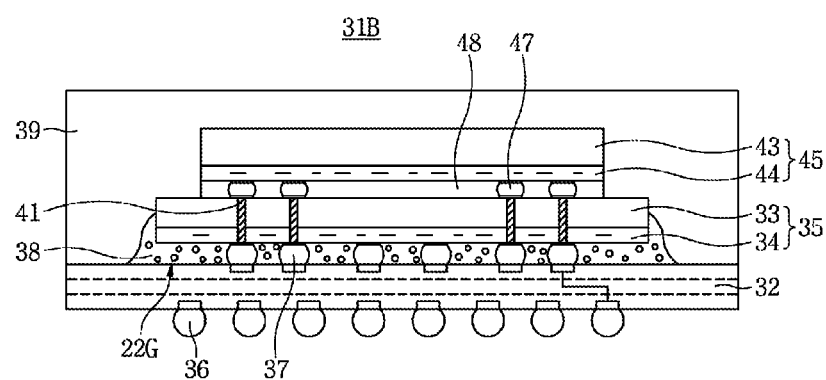
FIGS. 17 to 29 are cross-sectional views illustrating a semiconductor package in accordance with embodiments of the inventive concept.

Referring to FIG. 17, a semiconductor package 31B may include a package substrate 32, a first semiconductor chip 35, a second semiconductor chip 45, and an encapsulant 39. First internal terminals 37 and a first adhesive film 38 may be formed between the first semiconductor chip 35 and the package substrate 32. The first adhesive film 38 may include an underfill layer. The first internal terminals 37 may be connected to first through electrodes 41 and the package substrate 32 through the first adhesive film 38. A plurality of granular filters 22G may be included in the first adhesive film 38. Each of the granular filters 22G may include a granular semiconductor formed of the same or substantially the same material as a first semiconductor substrate 33 or second semiconductor substrate 43. As discussed above, the granular semiconductor may be one or more silicon granules that may include, for instance, a single silicon particle or multiple silicon particles clustered together. At least some of the granular filters 22G may be spaced apart from each other.

Figure 18:
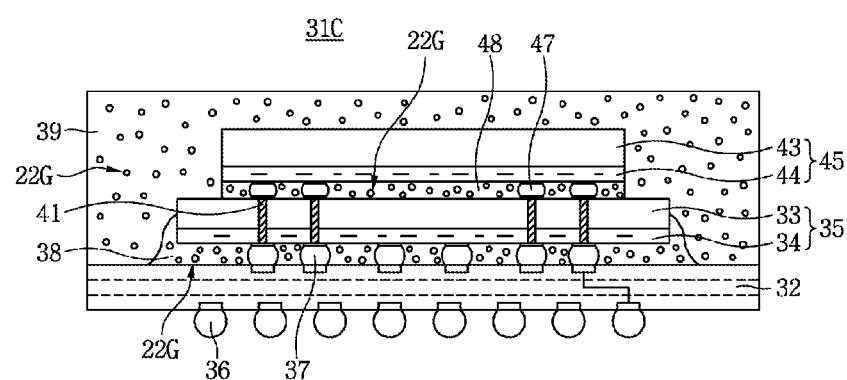

Referring to FIG. 18, a semiconductor package 31C may include a package substrate 32, a first semiconductor chip 35, a second semiconductor chip 45, and an encapsulant 39. First internal terminals 37 and a first adhesive film 38 may be formed between the first semiconductor chip 35 and the package substrate 32. The first adhesive film 38 may include an underfill layer. Second internal terminals 47 and a second adhesive film 48 may be formed between the first semiconductor chip 35 and the second semiconductor chip 45. A plurality of granular filters 22G may be included in the second adhesive film 48, the first adhesive film 38, and the encapsulant 39. Each of the granular filters 22G may include a granular semiconductor formed of the same or substantially the same material as a first semiconductor substrate 33 or second semiconductor substrate 43.

Figure 19:
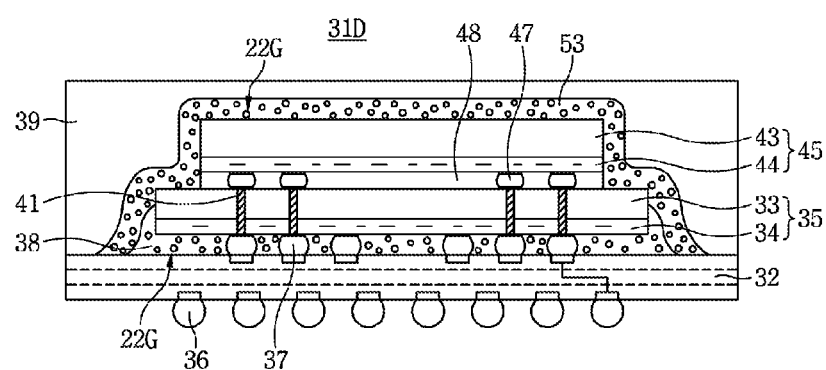

Referring to FIG. 19, a semiconductor package 31D may include a package substrate 32, a first semiconductor chip 35, a second semiconductor chip 45, a first coating film 53, and an encapsulant 39. First internal terminals 37 and a first adhesive film 38 may be formed between the first semiconductor chip 35 and the package substrate 32. The first adhesive film 38 may include an underfill layer. The first coating film 53 may cover the first semiconductor chip 35 and the second semiconductor chip 45. The first coating film 53 may cover upper and side surfaces of the first semiconductor chip 35 and the second semiconductor chip 45. The encapsulant 39 may cover the first coating film 53. A plurality of granular filters 22G may be included in the first adhesive film 38 and the first coating film 53. At least some of the granular filters 22G may include a granular semiconductor formed the same or substantially the same material as a first semiconductor substrate 33 or second semiconductor substrate 43.

Figure 20:
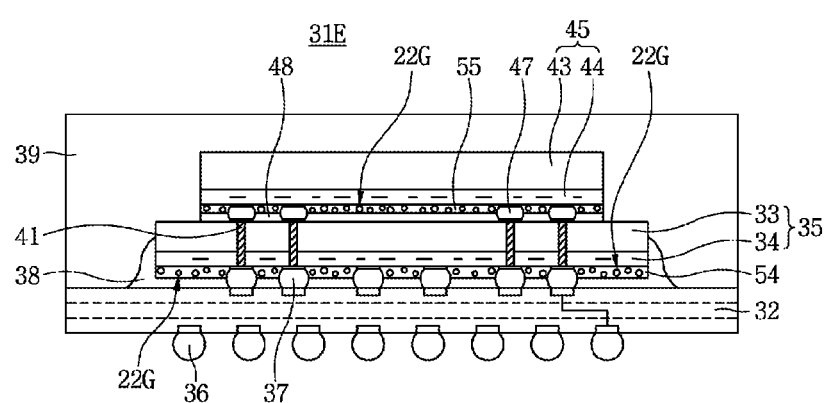

Referring to FIG. 20, a semiconductor package 31E may include a package substrate 32, a first semiconductor chip 35, a second semiconductor chip 45, and an encapsulant 39. First internal terminals 37, a first adhesive film 38, and a second coating film 54 may be formed between the first semiconductor chip 35 and the package substrate 32. The first adhesive film 38 may include an underfill layer. The second coating film 54 may be formed between the first adhesive film 38 and the first semiconductor chip 35. The second coating film 54 may be in contact with the first adhesive film 38 and the first semiconductor chip 35.

Second internal terminals 47 and a second adhesive film 48, and a third coating film 55 may be formed between the first semiconductor chip 35 and the second semiconductor chip 45. The third coating film 55 may be formed between the second adhesive film 48 and the second semiconductor chip 45. The third coating film 55 may be in contact with the second adhesive film 48 and the second semiconductor chip 45. The second coating film 54 and the third coating film 55 may include photosensitive polyimide (PSPI). A plurality of granular filters 22G may be included in the second coating film 54 and the third coating film 55. At least some of the granular filters 22G may include a granular semiconductor formed of the same or substantially the same material as a first semiconductor substrate 33 or second semiconductor substrate 43.

Figure 21:
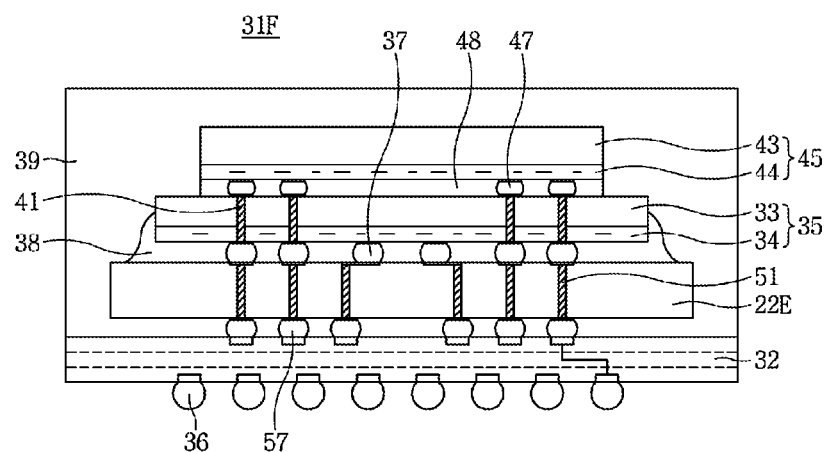

Referring to FIG. 21, a semiconductor package 31F may include a package substrate 32, a plate-shaped filter 22E, a first semiconductor chip 35, a second semiconductor chip 45, and an encapsulant 39. Second through electrodes 51 passing through the plate-shaped filter 22E may be formed. The plate-shaped filter 22E may be formed between the package substrate 32 and the first semiconductor chip 35. Third internal terminals 57 may be formed between the plate-shaped filter 22E and the package substrate 32. The third internal terminals 57 may include a solder ball or a conductive bump. First internal terminals 37 and a first adhesive film 38 may be formed between the first semiconductor chip 35 and the plate-shaped filter 22E.

The plate-shaped filter 22E may include a plate-shaped semiconductor formed of the same or substantially the same material as a first semiconductor substrate 33 or second semiconductor substrate 43. The plate-shaped filter 22E may have a greater thickness than the first semiconductor substrate 33 or the second semiconductor substrate 43. The plate-shaped filter 22E may have a larger horizontal width than the first semiconductor substrate 33 and the second semiconductor substrate 43.

Figure 22:
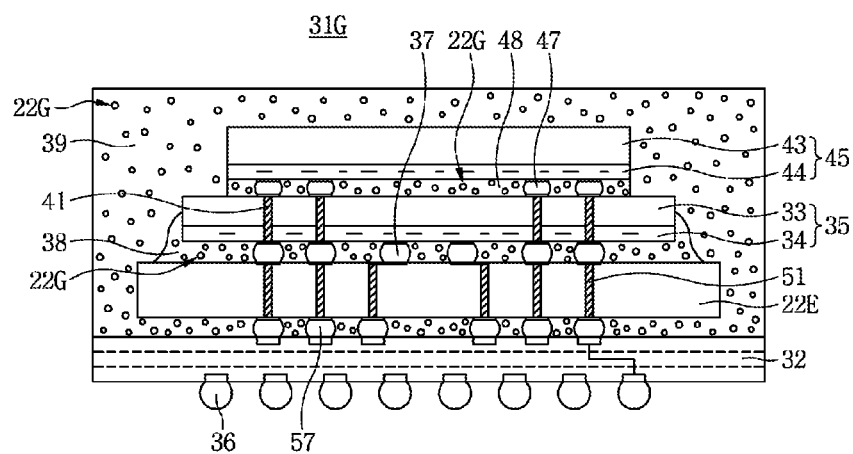

Referring to FIG. 22, a semiconductor package 31G may include a package substrate 32, a plate-shaped filter 22E, a first semiconductor chip 35, a second semiconductor chip 45, and an encapsulant 39. Second through electrodes 51 may be formed to pass through the plate-shaped filter 22E. The plate-shaped filter 22E may be formed between the package substrate 32 and the first semiconductor chip 35. Third internal terminals 57 may be formed between the plate-shaped filter 22E and the package substrate 32. The third internal terminals 57 may include a solder ball or a conductive bump. First internal terminals 37 and a first adhesive film 38 may be formed between the first semiconductor chip 35 and the plate-shaped filter 22E.

The plate-shaped filter 22E may include a plate-shaped semiconductor formed of the same or substantially the same material as a first semiconductor substrate 33 or second semiconductor substrate 43. A plurality of granular filters 22G may be included in a first adhesive film 38, a second adhesive film 48, and the encapsulant 39. Each of the granular filters 22G may include a granular semiconductor formed of the same or substantially the same material as the first semiconductor substrate 33 or the second semiconductor substrate 43.

Figure 23:
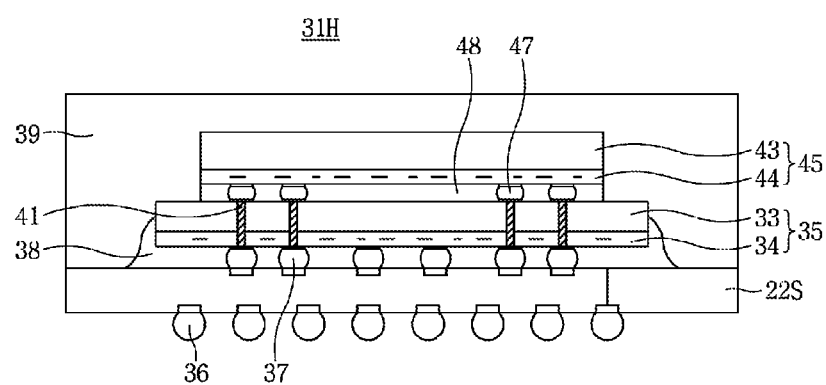

Referring to FIG. 23, a semiconductor package 31H may include a package substrate 22S, a first semiconductor chip 35, a second semiconductor chip 45, and an encapsulant 39. The package substrate 22S may include a plate-shaped semiconductor formed of the same or substantially the same material as a first semiconductor substrate 33 or second semiconductor substrate 43.

Figure 24:
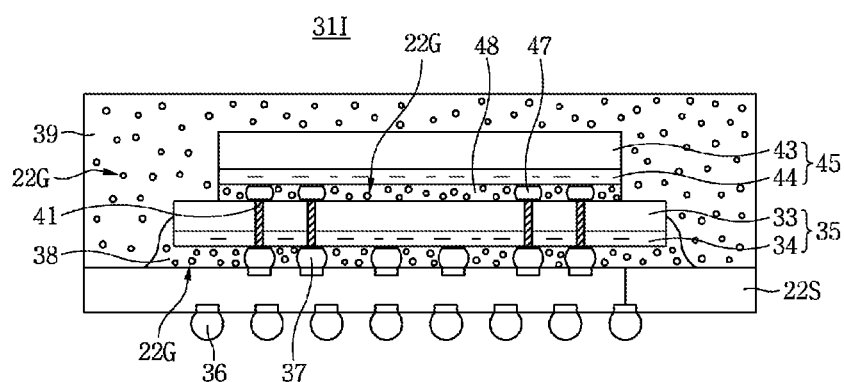

Referring to FIG. 24, a semiconductor package 31I may include a package substrate 22S, a first semiconductor chip 35, a second semiconductor chip 45, and an encapsulant 39. The package substrate 22S may include a plate-shaped semiconductor formed of the same or substantially the same material as a first semiconductor substrate 33 or second semiconductor substrate 43. A plurality of granular filters 22G may be included in the first adhesive film 38, a second adhesive film 48, and the encapsulant 39. Each of the granular filters 22G may include a plate-shaped semiconductor formed of the same or substantially the same material as the first semiconductor substrate 33 or second semiconductor substrate 43.

Figure 25:
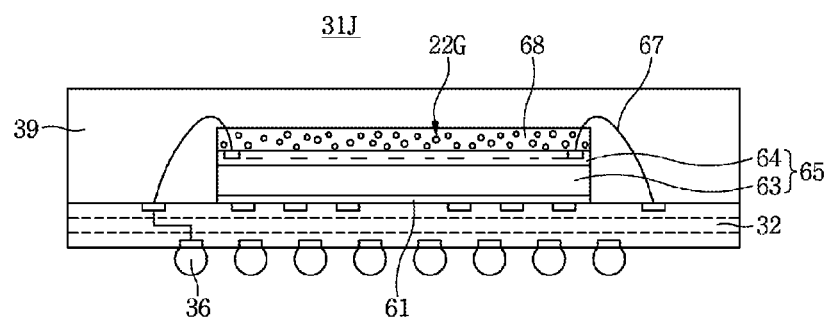

Referring to FIG. 25, a semiconductor package 31J may include a package substrate 32, a third semiconductor chip 65, and an encapsulant 39. The third semiconductor chip 65 may include a third semiconductor substrate 63 and a third active region 64 on the third semiconductor substrate 63. A plurality of active and/or passive devices and insulating layers may be formed in the third active region 64. A third adhesive film 61 may be formed between the third semiconductor substrate 63 and the package substrate 32. Fourth internal connectors 67 may be formed between the third active region 64 and the package substrate 32. The fourth internal connectors 67 may include a bonding wire, a beam lead, a conductive tape, or a combination thereof.

A fourth coating film 68 may be formed on the third active region 64. The encapsulant 39 may cover the fourth coating film 68. The fourth coating film 68 may include PSPI. In some embodiments, the fourth coating film 68 may cover only the top surface of the third semiconductor chip 65. A plurality of granular filters 22G may be included in the fourth coating film. Each of the granular filters 22G may include a granular semiconductor formed of the same or substantially the same material as the third semiconductor substrate 63.

Figure 26:
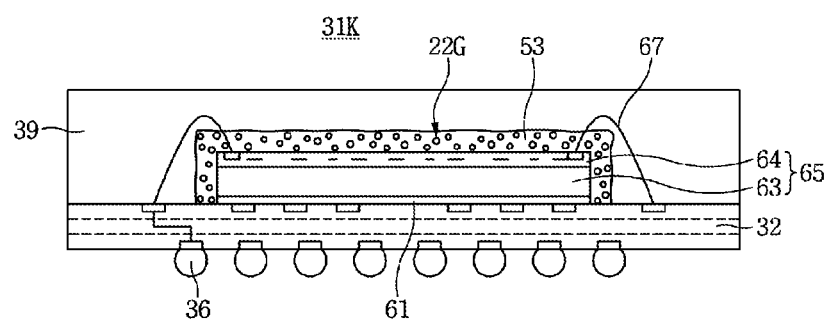
Figure 27:
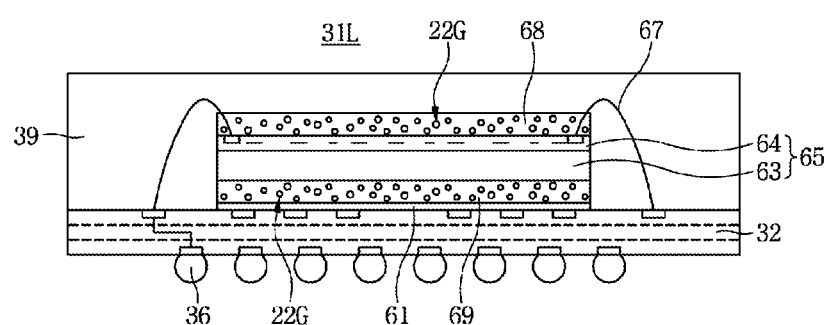

Referring to FIG. 26, a semiconductor package 31K may include a package substrate 32, a third semiconductor chip 65, and an encapsulant 39. A first coating film 53 may cover the top and side surfaces of the third semiconductor chip 65. A plurality of granular filters 22G may be included in the first coating film 53. Each of the granular filters 22G may include a granular semiconductor formed of the same or substantially the same material as the third semiconductor substrate 63.

Referring to 27, a semiconductor package 31L may include a package substrate 32, a third semiconductor chip 65, and an encapsulant 39. A third adhesive film 61 and a fifth coating film 69 may be formed between third semiconductor substrate 63 and the package substrate 32. The fifth coating film 69 may be disclosed between the third semiconductor substrate 63 and the third adhesive film 61. The fifth coating film 69 may be in contact with the third semiconductor substrate 63 and the third adhesive film 61. A fourth coating film 68 may be formed on a third active region 64. The encapsulant 39 may cover the fourth coating film 68. The fourth coating film 68 and the fifth coating film 69 may include PSPI.

A plurality of granular filters 22G may be included in the fourth coating film and the fifth coating film. Each of the granular filters 22G may include a granular semiconductor formed of the same or substantially the same material as the third semiconductor substrate 63.

Figure 28:
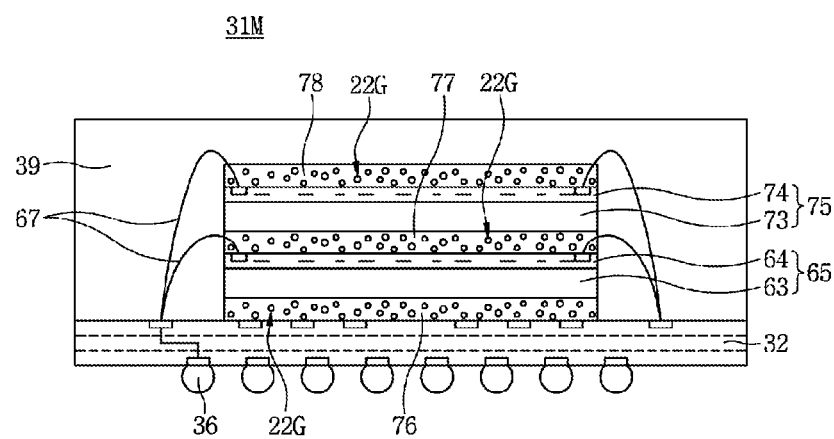

Referring to FIG. 28, a semiconductor package 31M may include a package substrate 32, a third semiconductor chip 65, a fourth semiconductor chip 75, and an encapsulant 39. The third semiconductor chip 65 may include a third semiconductor substrate 63 and a third active region 64 on the third semiconductor substrate 63. A fourth adhesive film 76 may be formed between the third semiconductor substrate 63 and the package substrate 32. The fourth semiconductor chip 75 may include a fourth semiconductor substrate 73 and a fourth active region 74 on the fourth semiconductor substrate 73. A fifth adhesive film 77 may be formed between the fourth semiconductor substrate 73 and the third semiconductor chip 65. A sixth coating film 78 may be formed on the fourth active region 74.

A plurality of granular filters 22G may be included in the fourth adhesive film 76, the fifth adhesive film 77, and the sixth coating film 78. Each of the granular filters 22G may include a granular semiconductor formed of the same or substantially the same material as the third semiconductor substrate 63 or the fourth semiconductor substrate 73.

Figure 29:
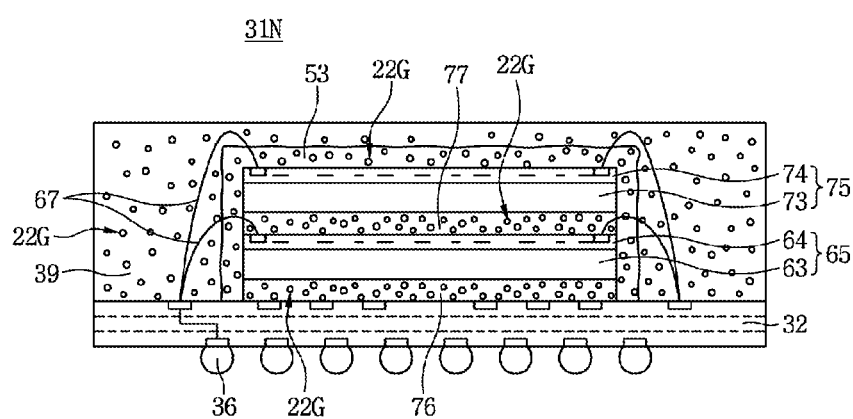

Referring to FIG. 29, a semiconductor package 31N may include a package substrate 32, a third semiconductor chip 65, a fourth semiconductor chip 75, and an encapsulant 39. A fourth adhesive film 76 may be formed between third semiconductor substrate 63 and the package substrate 32. A fifth adhesive film 77 may be formed between a fourth semiconductor substrate 73 and the third semiconductor chip 65. A first coating film 53 may be formed on the fourth active region 74. The first coating film 53 may cover top and side surfaces of the third semiconductor chip 65 and the fourth semiconductor chip 75.

A plurality of granular filters 22G may be included in the first coating film 53, the fourth adhesive film 76, the fifth adhesive film 77, and the encapsulant 39. Each of the granular filters 22G may include a granular semiconductor formed of the same or substantially the same material as the third semiconductor substrate 63 or the fourth semiconductor substrate 73.

Figure 30:
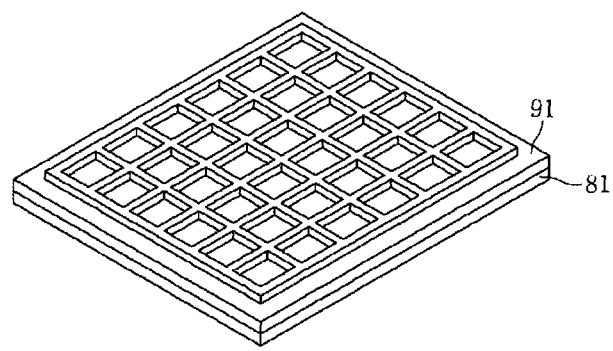
FIG. 30 is a perspective view illustrating a tray in accordance with embodiments of the inventive concept.
Figure 31:
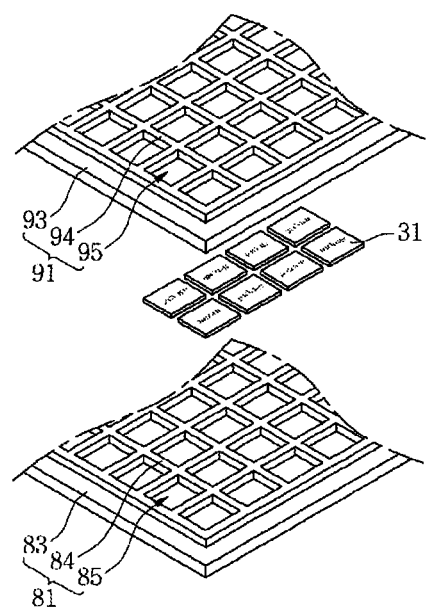
FIG. 31 is an exploded perspective view of FIG. 30.

FIG. 30 is a perspective view illustrating a tray in accordance with some embodiments of the inventive concepts, and FIG. 31 is an exploded perspective view of FIG. 30. FIGS. 32 to 38 are cross-sectional views of a tray in accordance with some embodiments of the inventive concepts. The tray in accordance with some embodiments of the inventive concept may serve as a container capable of housing a semiconductor package.

Referring to FIGS. 30 and 31, a second tray 91 may be stacked on a first tray 81. The first tray 81 may include a first lower plate 83, first partition walls 84, and first cavities 85. The second tray 91 may include a second lower plate 93, second partition walls 94, second cavities 95. A semiconductor package 31 may be stacked between the first tray 81 and the second tray 91. The semiconductor package 31 may be inserted into the first cavity 85.

The first partition walls 84 may be formed on the first lower plate 83. Side surfaces of the first partition walls 84 may define each of the first cavities 85 with upper surfaces of the first lower plate 83. For example, the bottom surfaces of the first cavities 85 may be defined by the upper surface of the first lower plate 83. The second tray 91 may have substantially the same or substantially the same configuration as the first tray 81.

The first tray 81 and the second tray 91 may include a semiconductor filter. The semiconductor filter may include the same or substantially the same material as the material that forms a semiconductor substrate in the semiconductor package 31. The semiconductor filter may include a plate-shaped semiconductor, a granular semiconductor, or a combination thereof.

Figure 32:
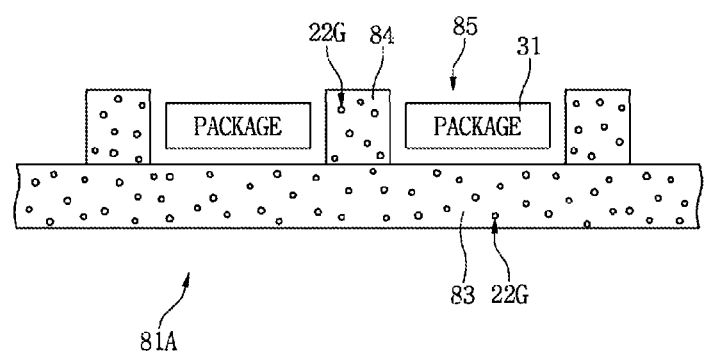
FIGS. 32 to 40 are cross-sectional views illustrating a tray with packages inserted in accordance with some embodiments of the inventive concept.

Referring to FIG. 32, a first tray 81A may include a first lower plate 83, first partition walls 84, and first cavities 85. A semiconductor package 31 may be inserted into one of the first cavities 85. A plurality of granular filters 22G may be mixed in or dispersed in the first lower plate 83 and the first partition walls 84. Each of the granular filters 22G may include a granular semiconductor formed of the same or substantially the same material as a semiconductor substrate in the semiconductor package 31. The first lower plate 83 may have a greater thickness than a semiconductor substrate in the semiconductor package 31.

Figure 33:
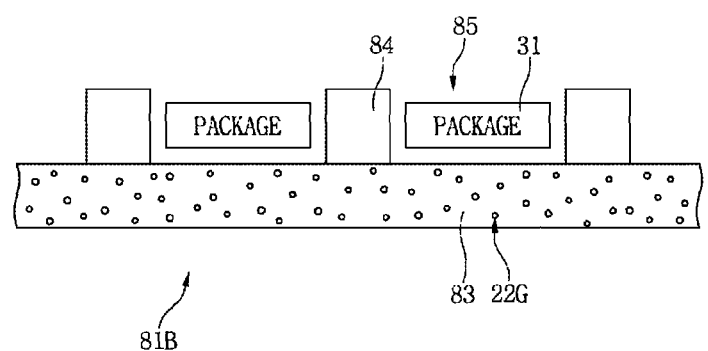

Referring to FIG. 33, a first tray 81B may include a first lower plate 83, first partition walls 84, and first cavities 85. A semiconductor package 31 may be inserted into one of the first cavities 85. A plurality of granular filters 22G may be included in the first lower plate 83. Each of the granular filters 22G may include a granular semiconductor formed of the same or substantially the same material as a semiconductor substrate in the semiconductor package 31.

Figure 34:
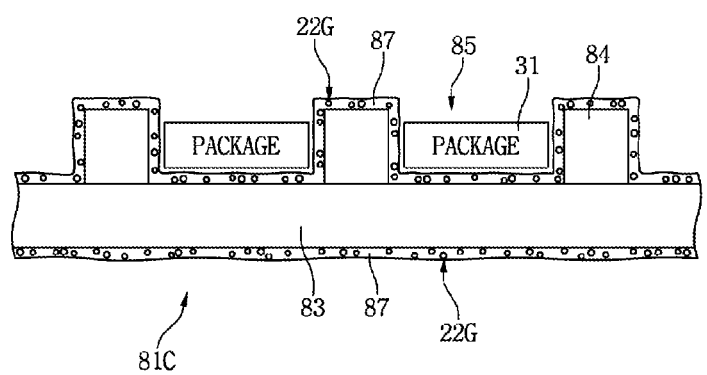

Referring to FIG. 34, a tray 81C may include a first lower plate 83, first partition walls 84, first cavities 85, and a first tray coating film 87. The first tray coating film 87 may cover surfaces of the first lower plate 83 and the first partition walls 84. The first tray coating film 87 may cover lower and upper surfaces of the first lower plate 83. The first tray coating film 87 may cover the bottom and sidewalls of the first cavity 85. A semiconductor package 31 may be inserted into the first cavity 85. A plurality of granular filters 22G may be included in the first tray coating film 87. Each of the granular filters 22G may include a granular semiconductor formed of the same or substantially the same material as a semiconductor substrate in the semiconductor package 31.

Figure 35:
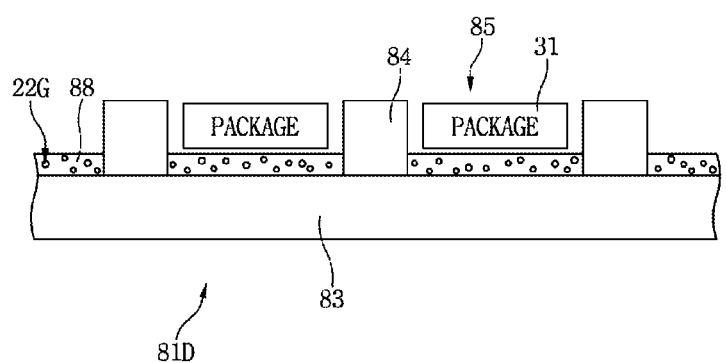

Referring to FIG. 35, a first tray 81D may include a first lower plate 83, first partition walls 84, first cavities 85, and a second tray coating film 88. The first tray coating film 87 may cover an upper surface of the first lower plate 83. The first tray coating film 87 may cover the bottom of the first cavity 85. A semiconductor package 31 may be inserted into the first cavity 85. A plurality of granular filters 22G may be included in the first tray coating film 87. Each of the granular filters 22G may include a granular semiconductor formed of the same or substantially the same material as a semiconductor substrate in the semiconductor package 31.

Figure 36:
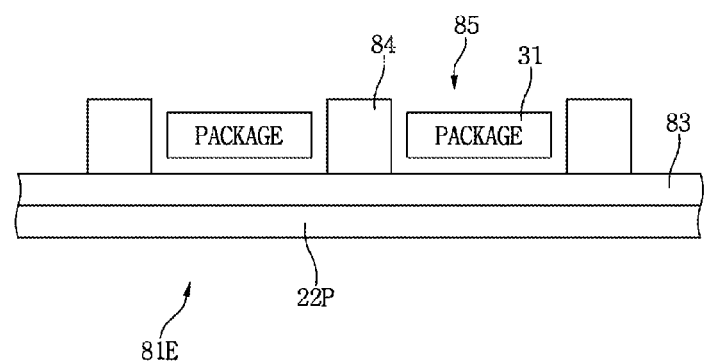

Referring to FIG. 36, a first tray 81E may include a first lower plate 83, first partition walls 84, first cavities 85, and a plate-shaped filter 22P. A semiconductor package 31 may be inserted into one of the first cavities 85. The plate-shaped filter 22P may be a plate-shaped semiconductor formed of the same or substantially the same material as a semiconductor substrate in the semiconductor package 31. The plate-shaped filter 22P may have a greater thickness than the semiconductor substrate in the semiconductor package 31. The plate-shaped filter 22P may be attached to the bottom of the lower plate 83.

Figure 37:
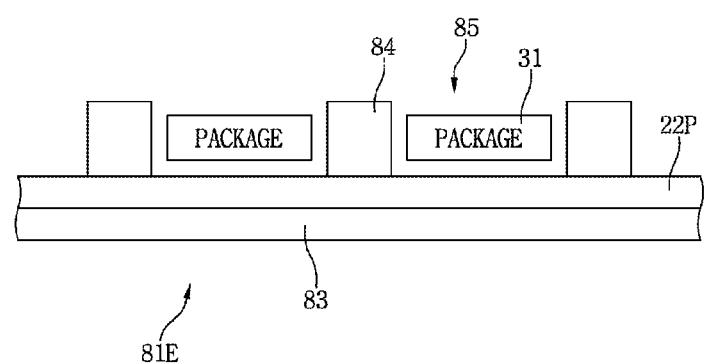

In another embodiment, as shown in FIG. 37, the plate-shaped filter 22P may be attached to an upper surface of the first lower plate 83.

Figure 38:
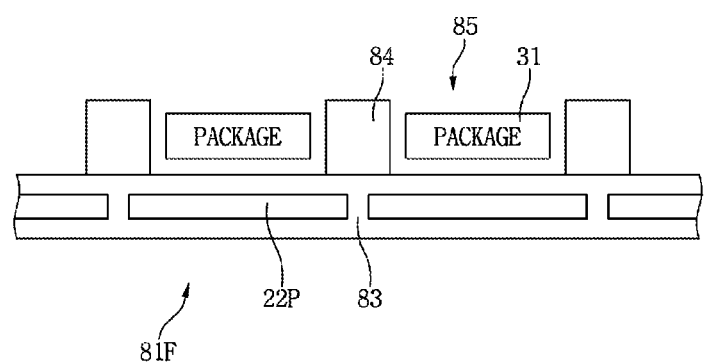

Referring to FIG. 38, a first tray 81F may include a first lower plate 83, first partition walls 84, first cavities 85, and a plurality of plate-shaped filters 22P. A semiconductor package 31 may be inserted into one of the first cavities 85. The plate-shaped filter 22P may include a plate-shaped semiconductor formed of the same or substantially the same material as a semiconductor substrate in the semiconductor package 31. The plurality of plate-shaped filter 22Ps may be disposed in the first lower plate 83.

Figure 39:
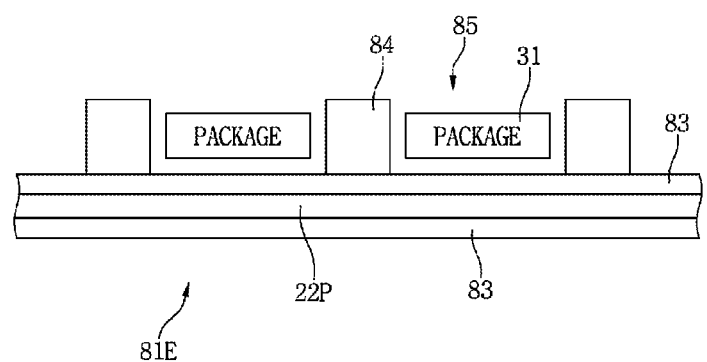

In another embodiment, as shown in FIG. 39, a single plate-shaped filter 22P, instead of multiple plate-shaped filters 22P, may be formed or disposed in the first lower plate 83.

Figure 40:
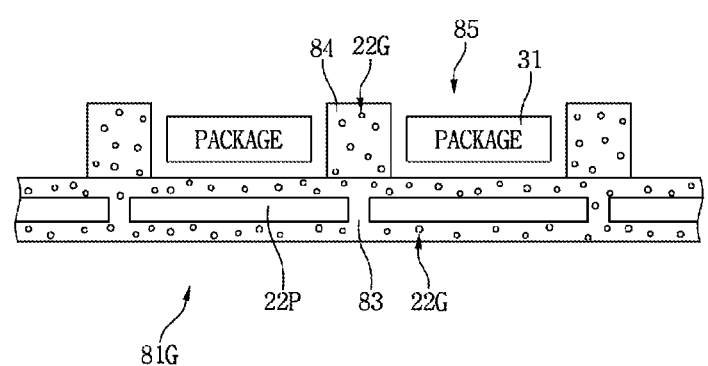

Referring to FIG. 40, a tray 81G may include a first lower plate 83, first partition walls 84, first cavities 85, and multiple plate-shaped filters 22P. A semiconductor package 31 may be inserted into one of the first cavities 85. The multiple plate-shaped filter 22P may be a plate-shaped semiconductor formed of the same or substantially the same material as a semiconductor substrate in the semiconductor package 31. The plate-shaped filter 22P may be inserted into the first lower plate 83. A plurality of granular filters 22G may be included in the first lower plate 83 and the first partition walls 84. Each of the granular filters 22G may include a granular semiconductor formed of the same or substantially the same material as a semiconductor substrate in the semiconductor package 31.

According to some embodiments of the inventive concepts, an X-ray system, a semiconductor package, and a tray having a semiconductor filter can be provided. The semiconductor filter can have the same or substantially the same material as a semiconductor substrate in the semiconductor package. The semiconductor filter can include a plate-shaped semiconductor, a granular semiconductor, or a combination thereof. The semiconductor filter can transmit X-rays in a first wavelength region which are required to obtain an image, and absorb X-rays in a second wavelength region which degrade the characteristics of a semiconductor chip. The X-ray system capable of substantially reducing degradation of a semiconductor device and obtaining a clear image can be implemented. The semiconductor package capable of substantially reducing degradation of the semiconductor device due to X-rays can be implemented. The tray for a semiconductor device capable of preventing degradation of the semiconductor device due to X-rays can be implemented.

The foregoing is illustrative of embodiments and is not to be construed as limiting thereof. Although a few embodiments have been described, those skilled in the art will readily appreciate that many modifications are possible in embodiments without materially departing from the novel teachings and advantages. Accordingly, all such modifications are intended to be included within the scope of this inventive concept as defined in the claims. In the claims, means-plus-function clauses are intended to cover the structures described herein as performing the recited function, and not only structural equivalents but also equivalent structures. Therefore, it is to be understood that the foregoing is illustrative of various embodiments and is not to be construed as limited to the specific embodiments disclosed, and that modifications to the disclosed embodiments, as well as other embodiments, are intended to be included within the scope of the appended claims.

What is claimed is:

1. An X-ray system, comprising:
an X-ray source;
a detector adjacent to the X-ray source;
a test specimen holder disposed between the X-ray source and the detector; and
a filter disposed between the X-ray source and the test specimen holder, the filter comprising a plate-shaped semiconductor, a granular semiconductor, or a combination thereof.

2. The X-ray system according to claim 1, wherein the filter includes Si, Ge, GaAs, InP, InGaAs, InGaAsP, or a combination thereof.

3. The X-ray system according to claim 1, wherein the filter comprises a plate-shaped semiconductor, and wherein the plate-shaped semiconductor includes a semiconductor wafer.

4. The X-ray system according to claim 1, wherein the test specimen holder is configured to load a semiconductor package having a semiconductor substrate therein, and wherein the filter includes the same or substantially the same material as a material that forms the semiconductor substrate.

5. The X-ray system according to claim 4, wherein the filter has a greater thickness than that of the semiconductor substrate.

6. The X-ray system according to claim 4, wherein the filter is included in the semiconductor package, and wherein the filter is disposed between the X-ray source and the semiconductor substrate.

7. The X-ray system according to claim 4, further comprising a first tray disposed on the semiconductor package, wherein the tray is disposed between the X-ray source and the semiconductor package, and wherein the filter is formed in the tray or on a surface of the tray.

8. The X-ray system according to claim 7, further comprising a second tray disposed below the semiconductor package such that the semiconductor package is disposed between the first tray and the second tray.

9. The X-ray system according to claim 1, wherein the filter further includes a metal filter including Zn, Fe, Al, Cu, Ni, Zr, Mo, Mn, V, or a combination thereof.

10. The X-ray system according to claim 9, wherein the metal filter is formed on one surface of the plate-shaped semiconductor.

11. The X-ray system according to claim 9, further comprising an insulating layer disposed between the metal filter and the plate-shaped semiconductor.

12. An X-ray system, comprising:
an X-ray source;
a detector adjacent to the X-ray source;
a test specimen holder disposed between the X-ray source and the detector; and
a filter disposed between the X-ray source and the test specimen holder, the filter comprising a semiconductor selected from a group consisting of Si, Ge, GaAs, InP, InGaAs, InGaAsP, and a combination thereof.

13. The X-ray system according to claim 12, wherein the test specimen holder is configured to load a semiconductor package having a semiconductor substrate therein, and wherein the filter includes the same or substantially the same material as a material that forms the semiconductor substrate.

14. The X-ray system according to claim 12, wherein the filter further includes a metal filter including Zn, Fe, Al, Cu, Ni, Zr, Mo, Mn, V, or a combination thereof.

* * * * *